United States Patent [19]

Burns

[11] 4,431,632
[45] Feb. 14, 1984

[54] INTERFACIAL COMPOSITION

[75] Inventor: Bobby C. Burns, Cambridge City, Ind.

[73] Assignee: Carson Chemicals, Inc., New Castle, Ind.

[21] Appl. No.: 381,867

[22] Filed: May 25, 1982

[51] Int. Cl.$^3$ ............................................. A61K 31/78
[52] U.S. Cl. ........................................ 424/81; 424/95; 424/180; 424/184; 424/224; 424/312; 424/343
[58] Field of Search .................. 424/81, 184; 128/521

[56] References Cited

U.S. PATENT DOCUMENTS

| | | | |
|---|---|---|---|
| Re. 29,814 | 10/1978 | Snyder | 424/81 |
| 3,310,052 | 3/1967 | Ward | 128/243 |
| 4,140,656 | 2/1979 | Mast | 424/81 X |

Primary Examiner—Leonard Schenkman
Attorney, Agent, or Firm—Hume, Clement, Brinks, Willian & Olds

[57] ABSTRACT

An interfacial composition suitable for topical application for animals, especially the vertebrates, comprising about 0.1 to 1 weight percent of an acrylic acid polymer, about 0.1 to 1 weight percent of a polyhydric alcohol, about 0.1 to 6 weight percent of an ethoxylated oleyl alcohol and oleyl ether phosphate, about 0.5 to 2 weight percent of a alkyl ester of a saturated fatty acid, about 0.1 to 5 weight percent of a lanolin derivative, about 0.1 to 3 weight percent of a dialkylpolysiloxane, about 0.1 to 10 weight percent of a neutralizing component, and the remainder water. Also disclosed is a method of using the aforementioned composition, comprising applying said composition over a predetermined area of the animal and, thereafter, covering said area for a time sufficient to reduce certain dimensional characteristics of the portion so covered. The subject composition, when applied with wrapping devices such as a plastic or rubberized cover, seemingly forms a heat reflecting and/or moisturizing barrier to aid in substantially reducing dimensional characteristics of the animal treated. The subject composition has been found to be effective in reducing the throat latch portion of horses.

10 Claims, No Drawings

INTERFACIAL COMPOSITION

BACKGROUND OF THE INVENTION

This invention relates to a preparation for topical applications and a process of using the same. In particular, the subject invention relates to compositions of matter containing certain gelling constituents in which specific oily and emulsifying fractions are incorporated and for their direct percutaneous application to selected areas to serve with associated devices as an interfacial chemical composition therewith.

Admittedly, various formulations have been used for topical applications having numerous active ingredients, said formulations taking the form of an ointment, liniment, or tincture for percutaneous application. As for most ointments, they can form sticky and unpleasant residues when applied and often may soil accompanying fabrics as well as leather goods. Moreover, the active ingredients in the ointment are not always fully available at the site of application and therefore useful and, when necessary, absorbable through cellular tissue. This is particularly noticeable at warmer temperatures where ointments are often susceptible to becoming somewhat unstable. With liniments and tinctures, on the other hand, active ingredients can often be percutaneously applied more effectively than in ointments; but the volatile active ingredients are often volatilized by the body temperature and thus fail to give any sustained medicinal efficacy or to play a role as an intimate constituent on the area where applied.

It is known that certain polymeric materials used in cosmetics and veterinary preparations, such as methyl cellulose and carboxymethyl cellulose may be applied to the tissues of an animal or human whereby a resinous-like layer is formed. However, usually an application of such material, especially in aqueous alcohol solutions, requires substantial quantities of such polymeric materials in order to impart the desired coating action to the resulting preparation. Additionally, when applied to the skin, the preparation requires a long time for the formation of a resinous layer, may be sticky to the touch, and may often be unstable.

It is in these percutaneous applications that proper formulation and topical application are to be sought, especially for the veterinary compositions that will adhere well, be stable, and form a suitable coating on the epidermis of an animal so as to form an insulating barrier layer thereover.

It has been discovered that certain compositions of matter seemingly aid, when applied to selected areas, in retaining caloric values or body heat. The composition acts as a barrier layer and, in conjunction with other devices, actually brings about weight reduction or a change in dimensional characteristics. It is not understood how this is actually accomplished. One theory is that the composition probably increases the state of hydration of the lower layer of the epidermis by altering the rate of diffusion of water from the yet lower epidermal and dermal layers whereby the rate of evaporation of water from the surface of the skin layer is greatly increased. The compositions herein disclosed and claimed have been found to substantially aid in retaining body heat in order to remove moisture and fatty tissues from the areas of the epidermis so treated, especially in conjunction with wrappings of the plastic or rubberized type.

SUMMARY OF THE INVENTION

The subject invention relates to an aqueous emulsion composition which utilizes a combination of ingredients that acts, when applied externally to tissues, as an interfacial barrier layer in conjunction with a covering or wrapping device. In particular, the compositions herein have been found useful for percutaneous application to selected areas of an animal's epidermis to aid in retaining their caloric values or body heat in order to reduce moisture and/or fatty tissues of the areas of the animals so treated. Broadly, the compositions of matter of the present invention are aqueous compositions comprising about 0.1 to 1 weight percent of a gelling agent such as acrylic acid polymers, about 0.1 to 1 weight percent of a polyhydric alcohol, an emulsifying fraction of about 0.1 to 6 weight percent of an (1) ethoxylated ether of oleyl alcohol and (2) esters of phosphoric acid and an ethoxylated ether of oleyl alcohol, an oily or lubricating fraction of about 0.1 to 5 weight percent of lanolin derivatives such as acetylated esters of the ethoxylated ether of lanolin alcohols, about 0.1 to 3 weight percent of a dialkylpolysiloxane, said lubricating fraction further including about 0.5 to 2 weight percent of an alkyl ester of a saturated fatty acid such as isopropyl palmitate, a neutralizing agent, said agent being present in about 0.1 to 10 weight percent, and the remainder water.

The method of the subject invention is addressed to applying, to an area of an animal for which one desires to eliminate moisture (e.g., the neck area of a horse), a thin uniform coating of the aforementioned composition and thereafter covering the coated portion with a plastic or rubberized wrap for a predetermined period of time and thereafter removing the wrap and rinsing or sponging the treated area.

DETAILED DESCRIPTION OF THE INVENTION

The present invention can be broadly defined as a composition of matter comprising about 0.1 to 1 weight percent of a gelling fraction of acrylic acid polymer, about 0.1 to 1 weight percent of a polyhydric alcohol, about 0.1 to 6 weight percent of an ethoxylated oleyl alcohol and oleyl ether phosphate, about 0.5 to 2 weight percent of a alkyl ester of a saturated fatty acid, about 0.1 to 5 weight percent of a lanolin derivative, about 0.1 to 3 weight percent of a dialkylpolysiloxane, about 0.1 to 10 weight percent of a basic component and the remainder water.

In a preferred embodiment, the gelling fraction is a 2 percent acrylic acid polymer solution which makes up above 90 to 98 percent of the total composition, while an emulsifying fraction, containing ethoxylated oleyl alcohol and oleyl ether phosphate, comprises about 0.5 to 10 percent of the total composition, and a lubricating or oily fraction which comprises about 0.5 to 5 percent of the total.

The gelling agents found suitable for the subject composition of the invention are those that may be generally described as interpolymers of a monomeric monoolefinic acrylic acid of the structure:

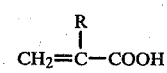

where R is a substituent selected from the class consisting of hydrogen and lower alkyl groups, and from about 0.1 to about 10 percent by weight based on the total monomers of a monomeric polyether or an oligosaccharide in which the hydroxyl groups which are modified are etherified with allyl groups, said polyether containing at least two allyl groups per oligosaccharide molecule.

The interpolymer can be formed varying greatly in molecular size, which may conveniently be evaluated in terms of viscosity of an aqueous solution, a 2 percent solution being generally suitable. The aforementioned interpolymers are commercially available and are marketed under the trade name Carbopol. These are described as being polymers of acrylic acid cross-linked with about 1 percent of a polyallyl ether of sucrose having an average of about 5.8 allyl groups for each sucrose molecule. These polymers have molecular weight in the order of magnitude of 1,000,000. Such polymers are available from the B. F. Goodrich Chemical Company and are sold under the trademark "Carbopol 934". Similarly, constituted products are designated "Carbopol 940: and "Carbopol 941".

The various Carbopols are distinguished from each other by the manufacturer on the basis of their viscosity. This is given in the following table:

|  | Brookfield RVF or RVT Viscosity, cP (20 rpm at 25° C., Neutralized Solns) | | | |
|---|---|---|---|---|
|  | % Sol. | Min. | Max. | Spindle |
| Carbopol 934 | 0.2 | 2,050 | 5,450 | 4 |
|  | 0.5 | 30,500 | 39,400 | 6 |
| Carbopol 940 | 0.2 | 15,000 | 35,000 | 6 |
|  | 0.5 | 40,000 | 60,000 | 7 |
|  | 1.0 | 50,000 | 85,000 | 7 |
| Carbopol 941 | 0.05 | 700 | 3,000 | 3 |
|  | 0.2 | 1,900 | 7,000 | 4 |
|  | 0.5 | 4,000 | 11,000 | 5 |

The polyhydric alcohol suitable for use in the compositions of the present invention, especially in forming the gelling fraction thereof, includes propylene glycol, ethylene glycol and glycerol and the like.

In a preferred method of making, say about 400 pounds of the gelling fraction of the subject composition, a two percent solution of the acrylic acid polymer is prepared by just placing in a suitable tank about 386 lbs., of deionized water followed by about 5 lbs., 8 oz. of propylene glycol and 8 lbs., of the acrylic acid copolymer (Carbopol 940). It has been found best to incorporate small amounts of germicides into this solution in order to preserve it against bacterial attack and the like. Satisfactory for this purpose has been found a combination of about 182 grams of methyl para-hydroxybenzoate and 45 grams of propyl para-hydroxybenzoate. In the preparation of the gelling solution, it has been found best to just place the water in a container and therafter to weigh out the propylene glycol in a separate container adding measured amounts of the hydroxybenzoates and heating to complete solution thereof. This solution is added to the water and thereafter with constant stirring the acrylic acid polymer is sprinkled into the solution and continually stirred until complete solution is obtained. The resulting solution is substantially a viscous, homogenous gel of clear-milky appearance.

The second fraction of the subject composition is essentially a combination, in a broad sense, of a lubricating and emulsifying portion. As for the emulsifying portion, it comprises an ethoxylated oleyl alcohol as well as an oleyl ether phosphate. In particular, the alcohol component is the ethoxylated ether of oleyl alcohol and conforms generally to the formula:

$$CH_3(CH_2)_7CH=CH(CH_2)_7CH_2(OCH_2CH_2)_nOH$$

where n has an average value of 3. The alcohol has a specific gravity of about 0.86 to 0.90. A commercially available ethoxylated oleyl alcohol is Volpo 3 (Croda, Inc., New York, N.Y.). As for the other constituent of the emulsifying portion found suitable for the subject invention, the esters formed generally rendering a complex mixture of esters, by the reaction of phosphoric acid and an ethoxylated ether of oleyl alcohol conforming to the formula:

$$CH_3(CH_2)_7C=CH(CH_2)_7CH_2(OCH_2CH_2)_nOH$$

where n has an average volume of 10. Again, a commercially available product is Crodophos N-10 neutral produced by Croda, Inc., New York, N.Y. In general, the ester has an iodine value of about 22 to about 32 and pH value of about 5.5 to 7.0.

The emulsifying portion may vary over a wide range, but preferably between about 0.1 and 6 weight percent of the total composition. In general, about 1 to about 2 weight percent of each has been found satisfactory.

The compositions of the subject invention are to include at least one alkyl ester of a saturated fatty acid in which the alkyl radical has from 2 to about 18 carbon atoms and the saturated fatty acid has from 12 to 20 carbon atoms. The role played by such alkyl ester is not fully understood but their presence seemingly enhances the subject composition. In general, the compositions of the subject invention should contain about 0.5 to about 2 weight percent of such alkyl esters. The preferred one is isopropyl palmitate. Other suitable esters may be used and include ethyl laurate, ethyl palmitate, ethyl stearate, isopropyl myristate, isopropyl stearate, butyl palmitate, butyl stearate, pentyl laurate, hexyl palmitate, octyl palmitate, dodecyl stearate, hexadecyl stearate, octodecyl myristate and the like.

The preferred allyl ester is the isopropyl palmitate, the ester produced by the reaction of isopropyl alcohol and palmitic acid.

In the oily or lubricating portion of the subject composition, certain lanolin derivatives are preferred. In this regard, the acetylated esters of the ethoxylated ether of lanolin alcohol have been found to be most satisfactory. Such derivatives have an average ethoxylation level of 10 moles ethylene oxide. In general, the lanolin alcohol is a mixture of organic alcohols derived from the hydrolysis of lanolin. A commercially available product, Solulan 98, produced by Amerchol, Edison, N.J., has been found to be most satisfactory, said product having a saponification value of between about 65 and 75, a specific gravity (25° C.) of about 1.035 and 1.055, and a pH of a 10 percent aqueous solution of about 5.0 to 7.5.

The polyalkylsiloxanes acceptable for use in the compositions of the present invention have the general formula:

$$-\!\!-\!\![R_2SiO]\!\!-\!\!-$$

wherein R is $C_1-C_4$ alkyl or phenyl and has a viscosity at 25° C., of from about 2,000 centistokes. A preferred polyalkylsiloxane is Silicone 200 Fluid supplied by the Dow Corning Corporation, having a viscosity at 25° C., of about 350 centistokes. In general, this fluid is a mixture of fully methylated linear siloxane polymer and blocked with trimethylsiloxy units. It conforms generally to the formula:

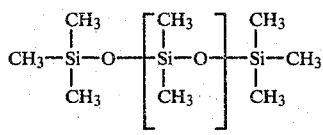

In general, the mixture of ingredients above-disclosed forms an aqueous solution in accordance with this invention having a somewhat acidic emulsion and should be somewhat neutralized with a basic component. Examples of components useful in this invention for neutralizing the combination of ingredients herein disclosed are the organic amines, including alkylamines such as methylamine, ethylamine and propylamine; dialkylamines such as dimethylamine, diethylamine and dipropylamine; trialkylamines such as trimethylamine, triethylamine and tripropylamine, alkanolamines such as methanolamine, ethanolamine and propanolamine; dialkanolamines such as dimethanolamine, diethanolamine and dipropanolamine and dibutanolamine; trialkanolamine such as trimethanolamine, triethanolamine, tripropanolamine and tributanolamine; and trimethylolaminomethane. Although the organic basic components are found most useful in composition of the subject invention, inorganic basic components are also useful and include sodium hydroxide, potassium hydroxide, ammonium hydroxide and the like.

The neutralization of the ingredients herein with the water-soluble basic component is generally so adjusted that the resulting preparation in the form of a gel has a pH proximate to neutrality; i.e., of 6.0 to 7.5.

The compositions may advantageously be prepared by just mixing the two percent polyacrylic acid (gelling fraction) first and thereafter adding the ethoxylated oleyl alcohol and oleyl ester phosphate, followed by the alkyl ester (isopropyl palmitate) and the lanolin derivative along with the dimethylpolysiloxane, the composition being finally neutralized by the water-soluble base.

A specific example embodying this invention follows and is not meant to be limiting. All percentages used herein in the specification and the claims are by weight unless otherwise specified.

EXAMPLE

The interfacial composition of this example can give a highly effective emulsion that, when applied to the neck of a horse in a thin coating and thereafter covered by a plastic or rubberized neck wrap, results in substantially reducing the size of the horse's neck without any need to exercise the horse as described in more detail hereinafter. It is believed that the subject composition physically aids in sealing off the plastic or rubberized wrapping by forming some sort of a barrier which greatly helps during the sweating process by retaining body heat necessary for the reduction of moisture and/or fatty tissue.

The following interfacial composition was made: A. A two percent polyacrylic acid homogeneous gel was prepared by mixing in the order given the following ingredients:

| | |
|---|---|
| 1. Water deionized | 386 lbs. |
| 2. Propylene glycol | 5 lbs., 8 oz. |
| 3. Methyl p-hydroxybenzoate | 182 gms. |
| 4. Propyl p-hydroxybenzoate | 45 gms. |
| 5. Polyacrylic acid (Carbopol 940) | 8 lbs. |

About 40 pounds of the two percent polyacrylic acid gel and 148 lbs. of water were added and mixed. B. In a separate container the following ingredients were added in the order set forth:

| | |
|---|---|
| 1. Ethoxylated Oleyl Alcohol (Volpo-3) | 3 lbs. |
| 2. Oleyl Ether Phosphate (Crodophos N-10 Neutral) | 3 lbs. |
| 3. Isopropyl Palmitate (Emerest 2316) | 2 lbs. |
| 4. Lanolin Derivative (Solulan 98) | 1 lb. |
| 5. Dimethylpolysiloxane (Dow 200 Fluid 100 cs) | 1 lb. |

The above composition (B) was added to the gel (A) with constant stirring and was thereafter neutralized with about 1 lb., 8 oz. of triethanolamine.

The method of application for the above-identified interfacial composition shall now be described. Each horse was first shampooed, rinsed, and wiped down prior to treatment. Each application of the composition was evenly applied, while the hair was still wet, to both sides of the neck from the mane down to the neck underline and from the jaw line to the slope of the shoulder. In general, between three to four ounces of the interfacial composition were applied to each horse.

After the composition was evenly applied to the area of the neck, a neck wrap was placed about the neck. The neck wrap used covered the neck completely from the jaw line and ears in front of the throat-latch back past the withers and down over the shoulders. When the neck wrap had been fitted over the neck, each horse was cross tied in its stall for one hour. At the end of the one-hour-treatment period, the neck wrap was removed and the treated area rinsed.

Control horses in this study received the same preparation and treatment as described above except that no interfacial composition was applied.

Measurements were taken for the neck circumference for each horse using a measuring tape at two locations on the neck; viz., the throat latch and the base of the neck. The base of the neck is that point immediately anterior to the apex of the wither down along the slope of the shoulder to the chest then up along the opposite shoulder slope back to the wither. An additional measurement was taken using X-ray calipers to measure the thickness of the neck, one side to the other. These measurements were taken at the throat latch, the base of the neck, and midway between the throat latch and the base of the neck.

Measurements were taken prior to treatment, at the end of the one-hour-treatment period (immediately after the neck wraps were removed) and again at one week after treatment. Measurements were repeated three times for neck circumference at each time interval for each horse and the average used to represent the required measurement for that point in time. The neck thickness measurements were taken once at each time interval. Each treatment was replicated a total of three times and involved a total of nine horses for the test. Note Table 1. Replicates one and two were comprised of stalled horses while replicate three for each treatment involved a reasonably fat brood mare.

Tables 2 and 3, summarized in Table 4 and indexed in Table 5, show that the interfacial composition in conjunction with the full-neck wrap affords rapid reduction of the neck circumference in the horses treated. It should be pointed out that this effect was more pronounced at the throat latch than at the base of the neck. From Table 6, these data show that the use of the composition was four times more effective after one hour in reducing the neck size in horses at the throat latch when compared to using only the neck wrap without said composition and under the same test regimen, in place for one hour. Although measurements taken at the base of the neck indicate similar effects in reducing neck circumference, these measurements were not as great in terms of reduced inches as those measurements taken in the throat latch area.

It may be added that the data further shows that by the end of one week post treatment, most of the inches removed from the neck had been, for the most part, regained. This observation was more noticeable in the control group than in the treated group.

The horses treated with the interfacial composition appeared to have tighter skins and somewhat smoother hair in the treated area immediately after the neck wraps were removed when compared to untreated control horses.

In conclusion, it is observed that when the interfacial composition is applied in conjunction with a full neck wrap, it is highly effective in reducing the neck circumference in horses after one hour of treatment. Specifically, the throat latch area of the horses treated with the subject composition was reduced four times more than the throat latch on horses treated only with the neck wrap. It will be appreciated that in displaying or showing horses, the animals are normally viewed standing and when viewed from the side, the throat latch area is noticeable and significant in judging and evaluating horses. Thus, any reduction in this normally thickened portion is favorably considered by those skilled in judging such animals.

TABLE 1

Description of horses used to study the effectiveness of the interfacial composition in reducing neck size in horses.

| Identification Number | Age | Weight | Sex | Maintenance System |
|---|---|---|---|---|
| INTERFACIAL COMPOSITION | | | | |
| 1422 | 8 yr | 1000 | Stallion | Stall |
| 0600 | 2 yr | 950 | Mare | Stall |
| 0111 | 16 yr | 1100 | Mare | Pasture |
| CONTROL | | | | |
| 0059 | 15 yr | 1000 | Gelding | Stall |
| 1429 | 4 yr | 1100 | Mare | Stall |
| 0110 | 13 yr | 1000 | Mare | Pasture |

TABLE 2

Neck circumference at both the throat latch and the base of the neck of horses before the following treatment with the interfacial composition.[1][2]

| Identification Number | Measurement Number | Throat Latch | | | Base of Neck | | |
|---|---|---|---|---|---|---|---|
| | | 0 | 1 hr | 1 wk | 0 | 1 hr | 1 wk |
| 1422 | 1 | 33.00 | 32.75 | 32.75 | 51.00 | 51.00 | 51.25 |
| | 2 | 33.25 | 32.00 | 32.50 | 52.25 | 51.75 | 51.75 |
| | 3 | 32.75 | 31.75 | 32.75 | 51.50 | 51.25 | 51.75 |
| | Total | 99.00 | 95.50 | 98.00 | 155.25 | 153.50 | 154.75 |
| | Total Reduction | | −3.50 | −1.00 | | −1.75 | −0.50 |
| | Average Reduction | | −1.17 | −0.33 | | −0.58 | −0.17 |
| 0060 | 1 | 31.00 | 30.00 | 30.75 | 51.00 | 50.50 | 51.00 |
| | 2 | 31.00 | 30.25 | 31.25 | 50.75 | 50.50 | 51.00 |
| | 3 | 31.00 | 30.00 | 31.25 | 50.75 | 50.25 | 50.50 |
| | Total | 93.00 | 90.25 | 93.75 | 152.50 | 151.25 | 152.50 |
| | Total Reduction | | −2.75 | +0.75 | | −1.25 | 0.0 |
| | Average Reduction | | −0.92 | +0.25 | | −0.42 | 0.0 |
| 0111 | 1 | 33.50 | 32.25 | 32.25 | 52.75 | 52.25 | 52.50 |
| | 2 | 33.25 | 32.00 | 33.00 | 53.00 | 52.50 | 52.50 |
| | 3 | 33.50 | 32.25 | 33.00 | 52.75 | 52.00 | 52.75 |
| | Total | 100.25 | 96.50 | 99.25 | 158.50 | 156.75 | 157.75 |
| | Total Reduction | | −3.75 | −1.00 | | −1.75 | −0.75 |
| | Average Reduction | | −1.25 | −0.33 | | −0.58 | −0.25 |

[1] All measurements were reported in inches.
[2] Each treatment required that the neck be covered with a full neck wrap during the one-hour-treatment phase.

TABLE 3

Neck circumference at both the throat latch and the base of the neck of horses[1][2] at indicated time intervals during the study.

| Identification Number | Measurement Number | Throat Latch | | | Base of Neck | | |
|---|---|---|---|---|---|---|---|
| | | 0 | 1 hr | 1 wk | 0 | 1 hr | 1 wk |
| 0059 | 1 | 32.25 | 31.50 | 31.75 | 49.00 | 49.00 | 49.00 |
| | 2 | 31.50 | 31.75 | 32.00 | 48.50 | 49.00 | 49.00 |
| | 3 | 32.00 | 31.50 | 31.50 | 49.00 | 48.50 | 49.00 |
| | Total | 95.75 | 94.75 | 95.25 | 146.50 | 146.00 | 147.00 |
| | Total Reduction | | −1.0 | −0.50 | | 0.0 | +0.50 |
| | Average Reduction | | −0.33 | −0.17 | | 0.0 | +0.17 |
| 1429 | 1 | 33.25 | 32.75 | 33.25 | 49.75 | 49.75 | 49.75 |
| | 2 | 32.75 | 33.00 | 33.25 | 50.00 | 49.75 | 50.00 |
| | 3 | 33.25 | 32.75 | 33.00 | 50.00 | 50.00 | 49.75 |
| | Total | 99.25 | 98.50 | 99.50 | 149.75 | 149.50 | 149.50 |

TABLE 3-continued

Neck circumference at both the throat latch and the base of the neck of horses[1][2] at indicated time intervals during the study.

| Identification Number | Measurement Number | Throat Latch 0 | 1 hr | 1 wk | Base of Neck 0 | 1 hr | 1 wk |
|---|---|---|---|---|---|---|---|
| | Total Reduction | | −0.75 | +0.25 | | −0.25 | −0.25 |
| | Average Reduction | | −0.25 | +0.08 | | −0.08 | −0.08 |
| 0110 | 1 | 34.25 | 34.00 | 34.00 | 51.25 | 51.00 | 51.00 |
| | 2 | 34.50 | 34.00 | 34.75 | 51.00 | 51.00 | 51.25 |
| | 3 | 34.25 | 34.25 | 34.25 | 51.25 | 51.25 | 51.00 |
| | Total | 103.00 | 102.25 | 103.00 | 153.50 | 153.25 | 153.25 |
| | Total Reduction | | −0.75 | 0.0 | | −0.25 | −0.25 |
| | Average Reduction | | −0.25 | 0.0 | | −0.08 | −0.08 |

[1] All measurements were reported in inches.
[2] Each treatment required that the neck be covered with a full neck wrap during the one-hour-treatment phase.

TABLE 4

Summary table showing the reduction in neck circumference at two locations on the neck with composition when compared to control horses.[1]

| Identification Number | Reduction in neck size (inches) | | | |
|---|---|---|---|---|
| | Throat Latch 1 hr | 1 wk | Base of Neck 1 hr | 1 wk |
| INTERFACIAL COMPOSITION | | | | |
| 1422 | 1.17 | 0.33 | 0.58 | 0.17 |
| 0062 | 0.92 | −0.25 | 0.42 | 0.00 |
| 0111 | 1.25 | 0.33 | 0.58 | 0.25 |
| Average | 1.11 | 0.14 | 0.53 | 0.14 |
| CONTROL | | | | |
| 0059 | 0.33 | 0.17 | 0.00 | −0.17 |
| 1429 | 0.25 | −0.08 | 0.08 | 0.08 |
| 0110 | 0.25 | 0.00 | 0.08 | 0.08 |
| Average | 0.28 | 0.03 | 0.05 | 0.003 |

[1] Each horse was required to wear a full neck wrap during the one-hour-treatment phase.

TABLE 5

Effectiveness index for interfacial composition when compared to the standard (untreated control) and the corresponding inches reduced (in parenthesis).

| Product | Reduction in neck size (inches) | | | |
|---|---|---|---|---|
| | Throat Latch 1 hr | 1 wk | Base of Neck 1 hr | 1 wk |
| INTERFACIAL COMPOSITION | | | | |
| Interfacial Composition (includes use of a neck wrap) | 4.0 (1.11") | 4.7 (0.14") | 10.6 (0.53") | 46.7 (0.14") |
| Control (Neck Wrap Only) | 1.0 (0.28") | 1.0 (0.03") | 1.0 (0.05") | 1.0 (0.003") |

TABLE 6

Thickness of the neck at three locations on the neck before and after treatment with the interfacial composition.

| Identification Number | Throat Latch | Mid Neck | Base of Neck |
|---|---|---|---|
| INTERFACIAL COMPOSITION | | | |
| 1422 Before | 9.125 | 9.75 | 11.75 |
| After (1 hour) | 9.125 | 9.75 | 11.625 |
| After (1 week) | 9.125 | 9.75 | 11.625 |
| 0060 Before | 8.625 | 9.375 | 11.50 |
| After (1 hour) | 8.625 | 9.375 | 11.50 |
| After (1 week) | 8.625 | 9.375 | 11.50 |
| 0111 Before | 9.50 | 9.875 | 11.875 |
| After (1 hour) | 9.50 | 9.875 | 11.875 |
| After (1 week) | 9.50 | 9.875 | 11.875 |
| CONTROL | | | |
| 0059 Before | 9.125 | 9.825 | 11.875 |

TABLE 6-continued

Thickness of the neck at three locations on the neck before and after treatment with the interfacial composition.

| Identification Number | Throat Latch | Mid Neck | Base of Neck |
|---|---|---|---|
| After (1 hour) | 9.125 | 9.875 | 11.750 |
| After (1 week) | 9.125 | 9.875 | 11.875 |
| 1429 Before | 9.625 | 10.750 | 12.625 |
| After (1 hour) | 9.500 | 10.750 | 12.625 |
| After (1 week) | 9.625 | 10.750 | 12.625 |
| 0110 Before | 9.625 | 10.875 | 13.125 |
| After (1 hour) | 9.500 | 10.875 | 13.000 |
| After (1 week) | 9.500 | 10.875 | 13.125 |

It will be understood that the specification and example herein are merely illustrative and not limiting of the present invention and that other embodiments within the spirit and scope of the invention will suggest themselves to those skilled in the art.

What is claimed is:

1. An interfacial composition of matter comprising about 0.1 to 1 weight percent of an acrylic acid polymer, said acrylic acid polymer being an interpolymer of a monomeric monoolefinic acrylic acid of the general structure:

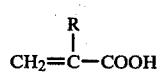

wherein R is a substituent selected from the class consisting of hydrogen and lower alkyl groups, and from about 0.1 to about 10 percent by weight based on the total monomers of a monomeric polyether of an oligosaccharide in which the hydroxyl groups which are modified are etherified with allyl groups, said polyether containing at least two allyl ether groups per oligosaccharide molecule, about 0.1 to 1 weight percent of a polyhydric alcohol selected from the group consisting of propylene glycol, ethylene glycol, and glycerol, about 0.1 to 6 weight percent of an ethoxylated oleyl alcohol and an oleyl ether phosphate, about 0.5 to 2 weight percent of alkyl ester selected from the group consisting of isopropyl palmitate, ethyl palmitate, butyl palmitate, hexyl palmitate, octyl palmitate, ethyl laurate, butyl stearate, hexadecylstearate, ethyl stearate, isopropyl myristate, isopropyl stearate, pentyl laurate, dodecyl stearate, octodecyl myristate and octodecyl palmitate, about 0.1 to 5 weight percent of a lanolin derivative, said derivative being an acetylated ester of an ethoxy ether of lanolin alcohol, the average ethoxylation being about 10 moles ethylene oxide, about 0.1 to 3 weight percent of a dialkylpolysiloxane, about 0.1 to 10 weight percent of a basic alkanolamine component and the remainder water.

2. The composition of claim 1 wherein the alkyl ester is isopropyl palmitate.

3. The composition of claim 1 wherein the dialkylpolysiloxane is dimethylpolysiloxane.

4. The composition of claim 1 wherein the composition includes esters of hydrobenzoic acid.

5. The composition of claim 4 wherein the esters of hydrobenzoic acid are methyl para-hydroxybenzoate and propyl para-hydroxybenzoate.

6. A method of reducing moisture and fatty tissues in an animal, said method comprising applying over a predetermined area of said animal an interfacial aqueous composition capable of forming a polymeric membrane over said area, said composition comprising about 0.1 to 1 weight percent of an acrylic acid polymer, said acrylic acid polymer being an interpolymer of a monomeric monoolefinic acrylic acid of the general structure:

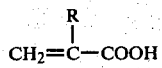

wherein R is a substituent selected from the class consisting of hydrogen and lower alkyl groups, and from about 0.1 to about 10 percent by weight based on the total monomers of a monomeric polyether of an oligosaccharide in which the hydroxyl groups which are modified are etherified with allyl groups, said polyether containing at least two allyl ether groups per oligosaccharide molecule, about 0.1 to 1 weight percent of a polyhydric alcohol selected from the group consisting of propylene glycol, ethylene glycol, and glycerol, about 0.1 to 6 weight percent of an ethoxylated oleyl alcohol and an oleyl ether phosphate, about 0.5 to 2 weight percent of an alkyl ester selected from the group consisting of isopropyl palmitate, ethyl palmitate, butyl palmitate, hexyl palmitate, octyl palmitate, ethyl laurate, butyl stearate, hexadecylstearate, ethyl stearate, isopropyl myristate, isopropyl stearate, pentyl laurate, dodecyl stearate, octodecyl myristate and octodecyl palmitate, about 0.1 to 5 weight percent of a lanolin derivative, said derivative being an acetylated ester of an ethoxy ether of lanolin alcohol, the average ethoxylation being about 10 moles ethylene oxide, about 0.1 to 3 weight percent of a dialkylpolysiloxane, about 0.1 to 10 weight percent of a basic alkanolamine component and the remainder water and covering said area for a time sufficient to retain the caloric value within the animal necessary for reduction of moisture and fatty tissues.

7. The method of claim 6 wherein the alkyl ester is isopropyl palmitate.

8. The method of claim 6 wherein the dialkylpolysiloxane is dimethylpolysiloxane.

9. The method of claim 6 wherein the composition includes esters of hydrobenzoic acid.

10. The method of claim 9 wherein the hydrobenzoic acid are methyl para-hydroxybenzoate and propyl para-hydroxybenzoate.

* * * * *

UNITED STATES PATENT AND TRADEMARK OFFICE
CERTIFICATE OF CORRECTION

PATENT NO. : 4,431,632

DATED : FEBRUARY 14, 1984

INVENTOR(S) : BOBBY C. BURNS

It is certified that error appears in the above-identified patent and that said Letters Patent is hereby corrected as shown below:

| Table 2. | Neck circumference at both the throat latch and the base of the neck of horses before and following treatment with the interfacial composition 1/ 2/ | | | | | | |
|---|---|---|---|---|---|---|---|
| Identification umber | Measurement Number | Throat Latch | | | Base of Neck | | |
| | | 0 | 1 hr | 1 wk | 0 | 1 hr | 1 wk |
| 1422 | 1 | 33.00 | 32.75 | 32.75 | 51.00 | 51.00 | 51.25 |
| | 2 | 33.25 | 32.00 | 32.50 | 52.25 | 51.75 | 51.75 |
| | 3 | 32.75 | 31.75 | 32.75 | 51.50 | 51.25 | 51.75 |
| | Total | 99.00 | 96.50 | 98.00 | 154.75 | 154.00 | 154.75 |
| Total Reduction | | | -2.50 | -1.00 | | -0.75 | 0.00 |
| Average Reduction | | | -1.17 | -0.83 | | -0.25 | 0.00 |
| 0060 | 1 | 31.00 | 30.00 | 30.75 | 51.00 | 50.50 | 51.00 |
| | 2 | 31.00 | 30.25 | 31.25 | 50.75 | 50.50 | 51.00 |
| | 3 | 31.00 | 30.00 | 31.25 | 50.75 | 50.25 | 50.50 |
| | Total | 93.00 | 90.25 | 93.25 | 152.50 | 151.25 | 152.50 |
| Total Reduction | | | -2.75 | +0.25 | | -1.25 | 0.00 |
| Average Reduction | | | -0.92 | +0.08 | | -0.42 | 0.00 |
| 0111 | 1 | 33.50 | 32.25 | 32.25 | 52.75 | 52.25 | 52.50 |
| | 2 | 33.25 | 32.00 | 33.00 | 53.00 | 52.50 | 52.50 |
| | 3 | 33.50 | 32.25 | 33.00 | 52.75 | 52.00 | 52.75 |
| | Total | 100.25 | 96.50 | 98.25 | 158.50 | 156.75 | 157.75 |
| Total Reduction | | | -3.75 | -2.00 | | -1.75 | -0.75 |
| Average Reduction | | | -1.25 | -0.67 | | -0.58 | -0.25 |

1/ All measurements were reported in inches.
2/ Each treatment required that the neck be covered with a full neck wrap during the one-hour-treatment phase.

UNITED STATES PATENT AND TRADEMARK OFFICE
CERTIFICATE OF CORRECTION

PATENT NO. : 4,431,632

DATED : February 14, 1984

INVENTOR(S) : BOBBY C. BURNS

It is certified that error appears in the above-identified patent and that said Letters Patent is hereby corrected as shown below:

Col. 8, in TABLE 1, second identification number, delete "0600" and insert --0060-- therefor.

Col. 8, TABLE 2, please substitute the entire table as submitted herewith.

In TABLE 3, please correct the error in the number for Identification Number 0059 in the 1 hr column under "Base of Neck" and delete "146.00" and substitue --146.50" therefor.

Signed and Sealed this

Twentieth Day of November 1984

[SEAL]

Attest:

Attesting Officer

GERALD J. MOSSINGHOFF

Commissioner of Patents and Trademarks